United States Patent
Östlund

(10) Patent No.: US 9,971,930 B2
(45) Date of Patent: May 15, 2018

(54) TEST MODULE FOR A FINGERPRINT SENSING DEVICE

(71) Applicant: Fingerprint Cards AB, Göteborg (SE)

(72) Inventor: Petter Östlund, Lund (SE)

(73) Assignee: FINGERPRINT CARDS AB, Göteborg (SE)

(*) Notice: Subject to any disclaimer, the term of this patent is extended or adjusted under 35 U.S.C. 154(b) by 0 days. days.

(21) Appl. No.: 15/725,331

(22) Filed: Oct. 5, 2017

(65) Prior Publication Data

US 2018/0106881 A1    Apr. 19, 2018

(30) Foreign Application Priority Data

Oct. 14, 2016 (SE) ...................................... 1651346

(51) Int. Cl.
| | |
|---|---|
| G06K 9/00 | (2006.01) |
| G01R 35/00 | (2006.01) |
| G06K 9/03 | (2006.01) |

(52) U.S. Cl.
CPC ......... G06K 9/0012 (2013.01); G01R 35/007 (2013.01); G06K 9/0002 (2013.01); G06K 9/00013 (2013.01); G06K 9/03 (2013.01); *A61B 2562/0233* (2013.01)

(58) Field of Classification Search
CPC ...... G06K 9/0002; G06K 9/03; G06K 9/0008; G06K 9/0012; G06K 9/0004; G06K 9/00013; A61B 2562/0233; H01L 51/5203; G01R 35/007
See application file for complete search history.

(56) References Cited

U.S. PATENT DOCUMENTS

| | | | | |
|---|---|---|---|---|
| 8,154,308 B2* | 4/2012 | Kormanyos | ........... | G01N 22/00 324/601 |
| 8,183,873 B2* | 5/2012 | Kobayashi | ......... | G06K 9/00053 324/658 |
| 8,798,947 B2* | 8/2014 | Prance | ................. | G06K 9/0002 702/65 |

(Continued)

FOREIGN PATENT DOCUMENTS

| | | |
|---|---|---|
| CN | 205388776 U | 7/2016 |
| CN | 106407057 A | 2/2017 |
| KR | 101482930 B1 | 1/2015 |

OTHER PUBLICATIONS

Swedish Search Report for Swedish Application No. 16513467 dated May 15, 2017, 2 pages.

*Primary Examiner* — Manav Seth

(74) *Attorney, Agent, or Firm* — RMCK Law Group PLC

(57) ABSTRACT

There is provided a test module for testing a fingerprint sensing device comprising: an electrically conductive bottom element comprising an exterior surface portion configured to contact a sensing surface of the fingerprint sensing device; an electrically conductive intermediate element, connected to the bottom element on a side opposing the exterior surface, the intermediate element comprising a flexible material enabling the bottom element to change alignment in response to an applied force occurring when the exterior surface is pressed against a surface being tilted with respect to the exterior surface of the bottom element; and a top element configured connect the test module to a test fixture. There is also provided a method for testing a fingerprint sensing device using the described test module.

19 Claims, 4 Drawing Sheets

(56) References Cited

U.S. PATENT DOCUMENTS

| | | | | |
|---|---|---|---|---|
| 8,953,848 B2* | 2/2015 | Ivanov | ............... | G06K 9/00013 |
| | | | | 382/115 |
| 9,524,415 B2* | 12/2016 | Liu | ..................... | G06K 9/0002 |
| 2009/0074256 A1* | 3/2009 | Haddad | ............. | G06K 9/00006 |
| | | | | 382/115 |
| 2012/0323513 A1* | 12/2012 | Prance | ................ | G06K 9/0002 |
| | | | | 702/65 |
| 2015/0070037 A1* | 3/2015 | Pragada | ............ | G01R 1/06705 |
| | | | | 324/754.03 |
| 2016/0019408 A1* | 1/2016 | Liu | ..................... | G06K 9/0002 |
| | | | | 382/124 |
| 2016/0300095 A1* | 10/2016 | Nilsson | ............... | G06K 9/0002 |

\* cited by examiner

TEST MODULE FOR A FINGERPRINT SENSING DEVICE

CROSS REFERENCE TO RELATED APPLICATIONS

This application claims priority to Sweden Application No. 1651346-7, filed on Oct. 14, 2016, the disclosure of which is incorporated herein by reference in its entirety.

FIELD

The present invention relates to a test module for testing a fingerprint sensing device.

BACKGROUND

Biometric sensors such as fingerprint sensors are becoming increasingly common in a wide range of applications such as computers, smartphones, smartcards and other applications where biometric identity verification is required. In particular, capacitive fingerprint sensors have been shown to provide accurate performance while being cost efficient and suitable for large scale manufacturing.

While fingerprint sensors often are manufactured in very large volumes with high manufacturing accuracy and high yield, it may still be desirable to test the produced sensors, thereby requiring efficient and automated test procedures. Moreover, when testing the sensors it is desirable to perform testing using a test structure which is as similar to a human finger as possible in order to replicate normal operating conditions for the sensor.

In particular, it is desirable to test the fingerprint sensor so that it is working as expected and that it captures images of sufficiently high quality. Since it is not practical to test the fingerprint sensor with an actual finger, a test rig can be used which comprises a rubber stamp or a rubber probe having a pattern allowing the functionality of the fingerprint sensor to be verified.

US2015/0070037 discloses a probe apparatus for testing a fingerprint sensing device where the device to be tested is located with a video camera, the probe is aligned with the device to be tested and the probe is lowered towards the sensor to contact the target. The probe apparatus comprises a housing in which the probe is mounted e.g. via a gimbal structure to allow the probe to move to adapt to misalignment of the contact surface.

SUMMARY

In view of above-mentioned and other drawbacks of the prior art, it is an object of the present invention to provide an improved test module for accurately testing a fingerprint sensing device.

According to a first aspect of the invention, there is provided a test module for testing a fingerprint sensing device comprising: an electrically conductive bottom element comprising an exterior surface portion configured to contact a sensing surface of the fingerprint sensing device; an electrically conductive intermediate element, connected to the bottom element on a side opposing the exterior surface, the intermediate element comprising a flexible material enabling the bottom element to change alignment in response to an applied force occurring when the exterior surface is pressed against a surface being tilted with respect to the exterior surface of the bottom element; and a top element configured connect the test module to a test fixture.

The described test module may advantageously be used in an automated test arrangement capable of sequential testing of fingerprint sensors. The test module will typically be substantially vertically aligned in a test arrangement in order to test a horizontally aligned sensing device, even though other arrangements are also possible. When testing, the test module is moved towards fingerprint sensing device so as to make contact with the sensing surface. Once the exterior surface portion of the bottom element is in contact with the sensing surface, a fingerprint image may be captured and further analyzed to verify a functionality of the fingerprint sensor.

A capacitive fingerprint sensing device often operates based on a principle where a varying electrical potential is provided to the finger placed on the sensor. The varying potential of the finger can then be detected by sensing elements in the fingerprint sensor, distinguishing fingerprint ridges and valleys, such that a fingerprint image can be acquired. Accordingly, to properly test the functionality of a fingerprint sensor the test module is electrically conductive such that a varying potential can be provided also to the test module.

The present invention is based on the realization that function testing of fingerprint sensors can be improved by providing an improved test module for testing a fingerprint sensing device where a flexible intermediate portion allows the test module to respond to an applied pressure similarly to a human finger. Thereby, the contact between the test module and the fingerprint sensor depends on the force with which the test module is pressed towards the fingerprint sensor in a manner similar to a finger. Furthermore, as a result of the flexible intermediate portion, the test module adapts the alignment of the bottom element to a tilt of the fingerprint sensing device. Herein, the tilt is referred to as a deviation from a horizontal plane in which the fingerprint sensing device is arranged. Thereby, a uniform contact between the test module and a sensing device can be achieved also for a sensing device being tilted. Moreover, the described test module has a simple construction and is therefor easy to manufacture at a low cost. Additionally, since the test module does not contain any moving parts it is durable and thereby capable of withstanding long term use without the need for maintenance or replacement.

According to one embodiment of the invention, the electrically conductive bottom element and/or the electrically conductive intermediate element may comprise a ground electrode configured to be connected to a corresponding ground electrode of a test fixture. Thereby, the test module can replicate the properties of a human finger which in general can be considered to be grounded, which allows the test module to behave as a finger when an electrical potential is provided to the test module. The test module may also be grounded by connecting an electrode of the bottom element to a corresponding ground electrode of a printed circuit board (PCB) or the like on which the fingerprint sensor is mounted.

According to one embodiment of the invention the intermediate element may be solid. The solid material will then comprise a flexible material which can be compressed if needed when the bottom element of the test module is pressed against a tilted surface.

Moreover, the intermediate element may advantageously consist of a single material, which simplifies manufacturing of the sensing module and which also provides homogeneous electrical and mechanical properties of the test module.

In another embodiment, the intermediate element may advantageously be hollow comprising flexible sidewalls. The desired flexibility of the test module can thereby be achieved by selecting an appropriate material and thickness of the sidewalls.

According to one embodiment of the invention, the flexible sidewalls may advantageously be electrically conductive.

According to one embodiment of the invention, the intermediate element may comprise an electrically conductive fluid, and the fluid may for example be a gel. Thereby, the desired flexibility of the test module can be achieved by selecting an appropriate fluidity of the fluid contained by the intermediate element. The intermediate element may be fully or partially filled with the conductive fluid.

Moreover, the electrical conductivity of the bottom element and of the intermediate element may advantageously correspond to the electrical conductivity of a finger. Thereby, the electrical properties of the test module can be made to mimic the electrical properties of a finger. Furthermore, the bottom element and the intermediate element may have different electrical properties, e.g. conductivity, corresponding to the different properties of different skin layers.

In one embodiment of the invention, the exterior surface portion of the bottom element may comprise a pattern configured to be detected by a fingerprint sensing device. Various test patterns can be used to test different aspects of the fingerprint sensing device. However, an entirely flat surface may also be used to test for example the uniformity of the sensor.

According to one embodiment of the invention, the exterior surface of the bottom portion may comprise a pattern replicating a fingerprint, thereby facilitating testing of various features of the fingerprint sensing device. However, the pattern may equally well comprise other patterns comprising ridges and valleys enabling testing of selected features of the sensing device.

According to one embodiment of the invention, the exterior surface of the bottom portion may comprise a plurality of different patterns, thereby making it possible to test various features of the sensing device using one and the same test module.

According to one embodiment of the invention, the intermediate portion may be flexible in a direction perpendicular to the exterior surface portion of the bottom element, which can be seen as the z-direction when the test module is vertically aligned. Again, it is desirable to replicate properties of a human finger which exhibits a certain degree of flexibility when pressed against a surface such as a sensing surface of a fingerprint sensing device.

According to one embodiment of the invention, the bottom portion may be flexible having an elastic modulus which is higher than an elastic modulus of the intermediate portion. Thereby, the intermediate portion is softer, i.e. has a higher flexibility, than the bottom portion. The purpose of this configuration of the respective elastic modulus is to allow the intermediate portion to flex in response to a force applied to the bottom portion while at the same time preventing the bottom portion from deforming when pressed against a surface. In particular, a pattern of the exterior surface of the bottom portion should not be deformed when pressed against a sensing surface of a fingerprint sensing device.

According to one embodiment of the invention, the intermediate element and/or the bottom element may comprise conductive rubber. Using a conductive rubber, desirable mechanical and electrical properties of the rubber materials can be selected for the intermediate element and the bottom element, respectively.

According to one embodiment of the invention, the test module may further comprise an electrically conductive film arranged between the bottom element and the intermediate element, wherein the electrically conductive film is configured to be connected to a ground electrode of a test fixture. As described above, it is desirable that at least the bottom element of the test module can be electrically grounded. By providing an electrically conductive film, such as a metal foil or the like, between the bottom element and the intermediate element and in electrical contact with the bottom element, the ground potential is homogeneous over the entire exterior surface of the bottom element. Thereby, the fingerprint sensor can be accurately tested without any non-uniformity introduced by the test module. Moreover, the electrically conductive film is configured to be connected to a ground electrode of a test fixture for example by means of a wire or similar conductive trace.

According to a second aspect of the invention, there is provided a method for testing a fingerprint sensing device using a test module comprising: an electrically conductive bottom element comprising a substantially flat exterior surface portion configured to contact a sensing surface of the fingerprint sensing device; an electrically conductive intermediate element, connected to the first portion on a side opposing the exterior surface, the second portion comprising a flexible material enabling the bottom element to change alignment in response to an applied force occurring when the exterior surface is pressed against a surface being tilted with respect to the exterior surface of the bottom element; and a top element configured connect the test module to a test fixture. The method comprises arranging a fingerprint sensing device below the test module; moving the test module towards the fingerprint sensing device such that the exterior surface portion of the bottom element makes contact with a sensing surface of the sensing device; and capturing an image using the fingerprint sensing device.

By means of the described method and test module, a fingerprint sensing device may be accurately tested even if the sensing device is tilted.

According to one embodiment of the invention, the method further comprises verifying that the image captured by the fingerprint sensing device corresponds to a surface pattern of an exterior surface the bottom element.

Additional effects and features of the second aspect of the invention are largely analogous to those described above in connection with the first aspect of the invention.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing an example embodiment of the invention, wherein.

DETAILED DESCRIPTION OF EXAMPLE EMBODIMENTS

In the present detailed description, various embodiments of the system and method according to the present invention are mainly described with reference to a capacitive fingerprint sensing device. However the described invention may also be applicable for other types of fingerprint sensing devices such as ultrasonic or optical fingerprint sensing devices.

Figure 1:
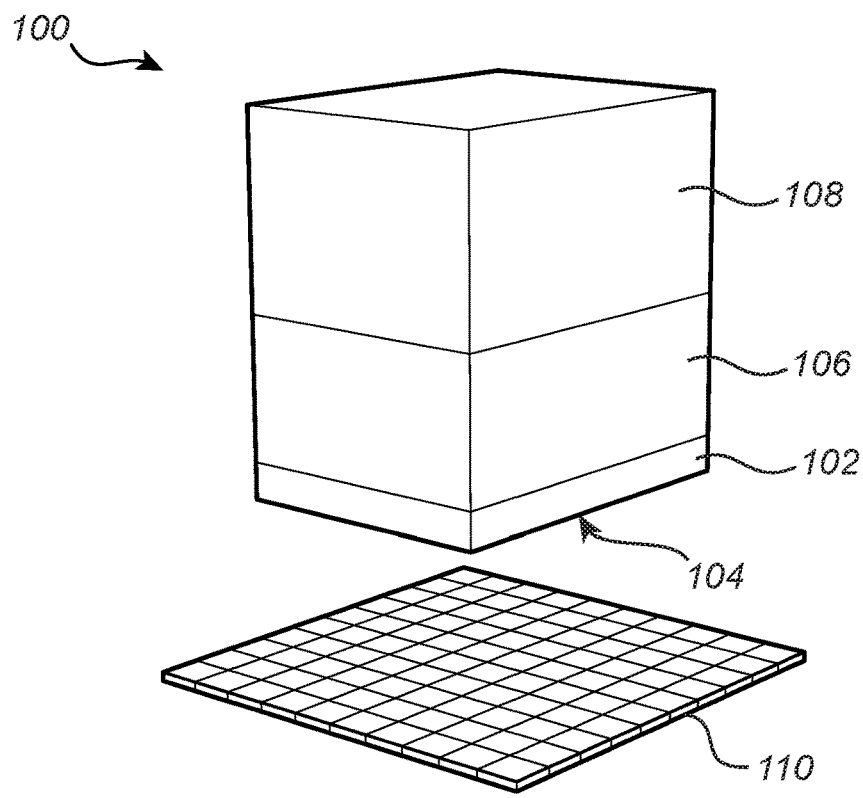
FIG. 1 schematically illustrates a test module according to an embodiment of the invention.

FIG. 1 schematically illustrates a test module 100 according to an embodiment of the invention. The test module comprises an electrically conductive bottom element 102 comprising an exterior surface portion 104 configured to contact a sensing surface of a fingerprint sensing device 110. The exterior surface portion 104 thus refers to the bottom surface of the test module 100, i.e. the surface facing the fingerprint sensing device 110.

The test module 100 further comprises an electrically conductive intermediate element 106, connected to the bottom element 102 on a side opposing the exterior surface 104. The intermediate element 106 comprises a flexible material enabling the bottom element 102 to change alignment in response to an applied force occurring when the exterior surface is pressed against a surface being tilted with respect to the exterior surface 104 of the bottom element 102. The test module further comprises a top element 108 configured connect the test module 100 to a test fixture. The elements 102, 106, 108 of the test module 100 may be fixed to each other for example by means of glue, or by using any other means known by the skilled person.

Moreover, even though the test module 100 is illustrated herein as having a square cross section, the test module may equally well have a cross section which is circular, oval, or any other suitable shape.

Figure 2:
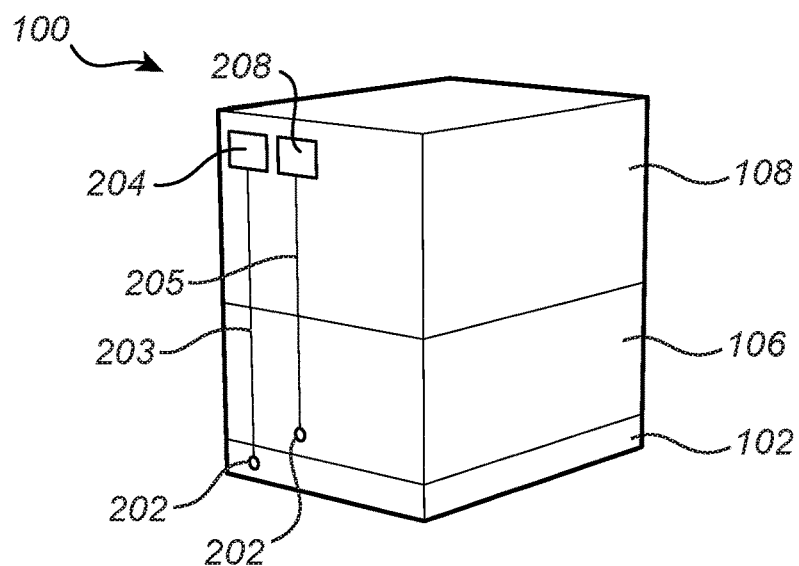
FIG. 2 schematically illustrates a test module according to an embodiment of the invention.

FIG. 2 schematically illustrates the test module 100 comprising a first electrode 202 configured to connect the bottom element 102 to a test fixture via a connection pad 204 on the top element. Optionally, the test module 100 may also comprise a second electrode 206 configured to connect the intermediate element 106 to a test fixture via a connection pad 208 on the top element. Depending on the thickness and electrical properties of the bottom element 102 it may be sufficient that only the bottom element 102 is connected to ground potential to achieve electrical properties similar to those of a human finger. The connecting elements 203, 205 connecting the bottom element and the intermediate element, respectively, to a test fixture may for example be a wire, which may or may not be shielded. Moreover, the connecting elements 203, 205, may be internal or external, and other suitable types of conductors may also be used.

However, even though the electrodes 202, 206 are configured to be connected to a corresponding ground electrode of test fixture such that the bottom element 102 and the intermediate elements 106 are grounded, the electrodes 202, 206 may also be used to provide a controlled potential to the test module 100 if desirable.

Figure 3:
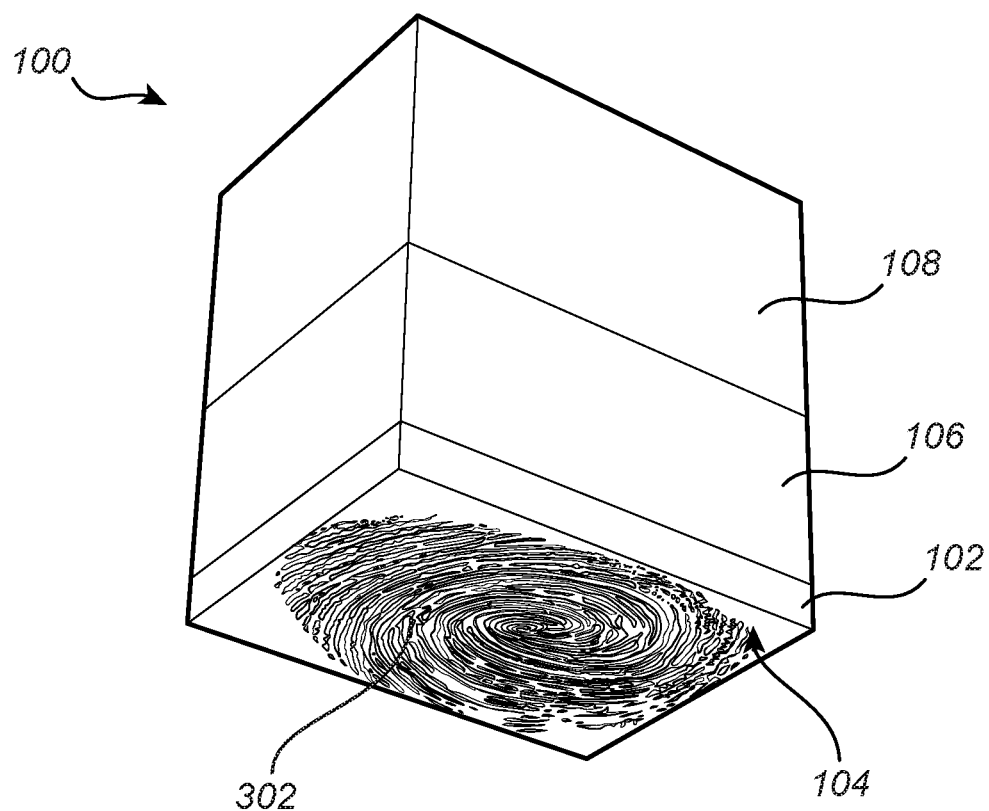
FIG. 3 schematically illustrates a test module according to an embodiment of the invention.

FIG. 3 schematically illustrates a test module 100 where the exterior surface 104 of the bottom element 102 comprises a pattern 302, here in the form of a fingerprint pattern 302. The pattern 302 is used to test a functionality of a fingerprint sensing device. The test module 100 may also be used with an entirely flat exterior surface, e.g. to test the uniformity of the fingerprint sensing device under circumstances where each pixel is supposed to provide the same response. I.e. the resulting captured image should be uniform. The test pattern may also comprise various geometrical shapes arranged and configured to test various featured of the sensing device.

Furthermore, the exterior surface is illustrated as being substantially flat on a macroscopic scale, when compared to the microscopic fingerprint pattern. However, the test surface may instead have a convex or otherwise curved exterior surface in order to replicate the shape of a human finger.

Figure 4:
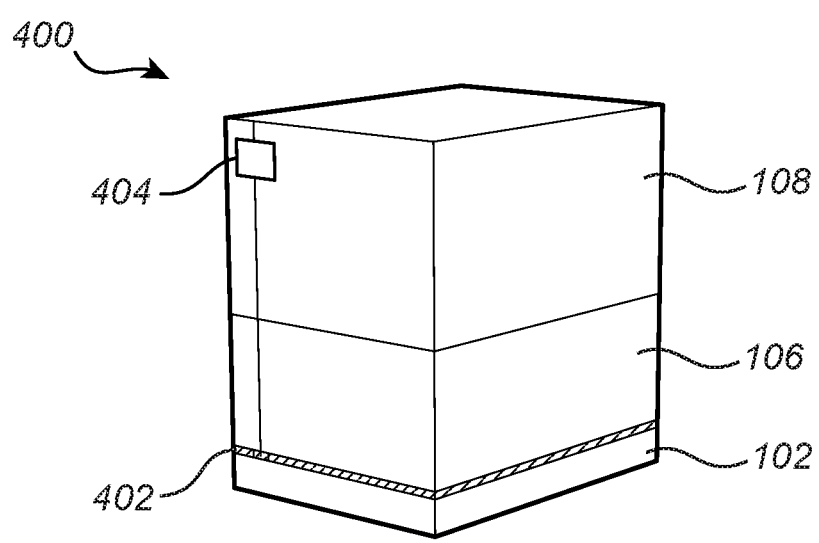
FIG. 4 schematically illustrates a test module according to an embodiment of the invention.

FIG. 4 schematically illustrates an embodiment of the test module 400 where an electrically conductive film 402 is located between the bottom element 102 and the intermediate element 106. The conductive film is configured to be connected to a test fixture by means of a connection pad 404 located on the top element 108. The conductive film 402 is in electrical contact with the bottom element 102 such that the bottom element 102 can be held at an electrical potential, e.g. ground, provided to the conductive film 402 by means of the connection pad 404. Moreover, the conductive film 402 may be either electrically connected to or insulated from the intermediate element 106.

Figure 5:
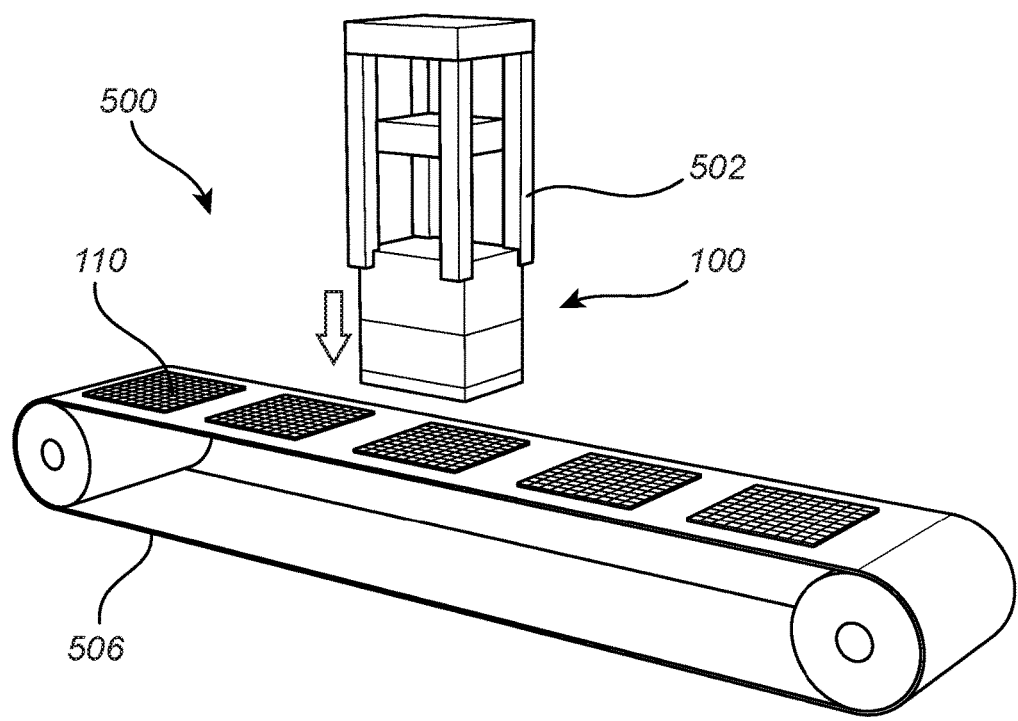
FIG. 5 schematically illustrates a test arrangement comprising a test module according to an embodiment of the invention.

FIG. 5 schematically illustrates a test arrangement 500 comprising a test fixture 502 in which the test module 100 is mounted. FIG. 5 further illustrates a plurality of fingerprint sensing devices 110 arranged on a conveyor belt 506.

For simplicity, the fingerprint sensing devices 110 are illustrated as individual fingerprint sensors 110. In practice, the fingerprint sensing devices may be tested at any point in the manufacturing and assembly process, from wafer scale testing to function testing when the finalized sensing device is arranged in an electronic device such as a smartphone. The test module 100 described herein may advantageously be used for testing at any production stage.

To perform the test, the test module 100 is moved towards the fingerprint sensing device 110 through a movement of the test fixture 502 such that the exterior surface 104 of the test module 100 comes into contact with the fingerprint sensing device 110. The interaction between the test module 100 and a fingerprint sensing device 110 is illustrated in further detail in FIGS. 6A-B where a test module is contacting a tilted fingerprint sensing device 110. It should be noted that the tilt is exaggerated to emphasize the general properties of the test module 100. The tilt is illustrated as a tilt about the xy-plane, i.e. a deviation from the xy-plane in the z-direction.

Figures 6A, 6B:
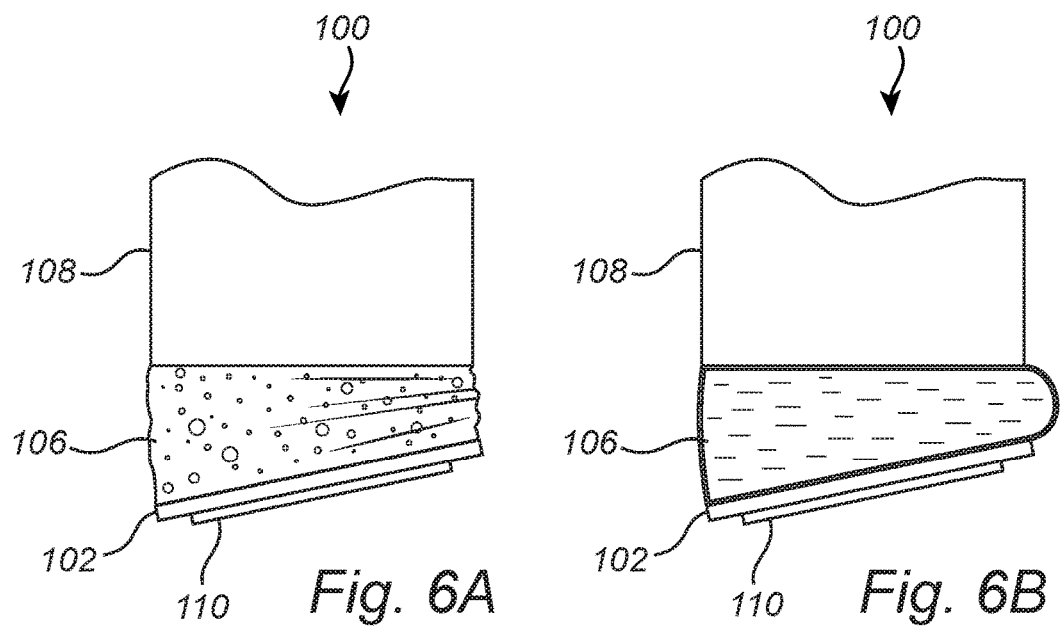
FIGS. 6A-6B schematically illustrates a test module according to an embodiment of the invention.

In case of a compressible intermediate element 106, the tilt is accommodated by a compressing of the portions of the intermediate element corresponding to the elevated portions of the sensing device 110 as illustrated in FIG. 6A. The intermediate element 106 may also comprise a non-compressible fluid such as a gel, in which case flexible sidewalls of the intermediate element 106 deforms to accommodate the tilt, as illustrated in FIG. 6B.

It is desirable that there is an even pressure between the bottom element 102 and the sensing device 110 to provide a uniform contact.

Thereby, the intermediate element 106 is configured to have a relatively low resulting elastic modulus, i.e. a low Young's modulus, such that it easily adapts its shape in response to a force applied on the bottom element 102. The bottom element 102 may also be flexible, although the Young's modulus of the bottom element should be sufficiently high such that a pattern on the exterior surface 104 is not deformed when the test module 100 is pressed against a sensing device.

Both a compressible solid intermediate element 106 as well as a hollow element 106 having flexible sidewalls may be made from a conductive rubber material.

The top element 108 is typically rigid and solid to reliably maintain the test module in place in the test fixture. However, the skilled person readily realizes that many different configurations of the top element are possible and within the scope of the present disclosure.

The test module 100 is here illustrates as having a larger footprint are than the fingerprint sensor which may be advantageous to ensure that the entire sensing area is covered even if the fingerprint sensing device should be translated in the xy-plane. Moreover, in applications where the fingerprint sensing device 110 is surrounded by or otherwise arranged adjacent to a conductive bezel, it is preferred that the test module covers also the bezel. The bezel may for example be used to provide a signal to the finger, where the signal in turn is detected by the fingerprint sensor to enable fingerprint imaging.

It is desirable to prevent electrical noise and other disturbances originating from the test fixture and the test arrangement from reaching the test module 100. Accordingly, the top element 108 being mounted in the test fixture 502 is advantageously made from an electrically insulating material such that at least the bottom element 102 is electrically insulated from the test fixture 502, or at least not shares a ground connection with the overall structure of the test fixture 502. The electrical connection to the bottom element 102, and possibly to the intermediate element 106, is thereby provided only by means of a controlled connection via the connection pads of the top element 108. Thereby, a dedicated, noise-free, ground connection can be provided. In another embodiment, the bottom element 106 may comprise an electrode on its exterior surface, where the electrode is configured to connect to a corresponding ground electrode located adjacent to the sensing surface of the fingerprint sensor. The ground electrode may for example be located on a PCB (not shown) on which the fingerprint sensing device 110 is mounted such that the ground connection is formed when the test module 100 is moved towards and in contact with the fingerprint sensing device 110. Thereby, disturbances from the test fixture 502 are prevented from reaching the fingerprint sensing device 110. Moreover, the ground connection may also be provided via the intermediate element.

Figure 7:
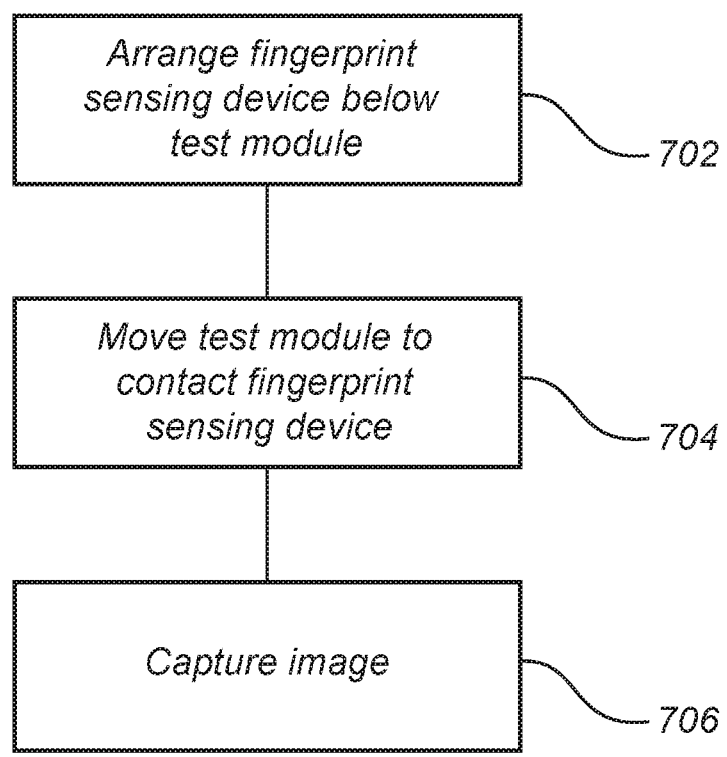
FIG. 7 is a flow chart outlining general steps of a method according to an embodiment of the invention.

FIG. 7 is a flow chart illustrating the general steps of a method according to an embodiment of the invention. The method outlined in FIG. 7 will be described with reference to FIG. 5 illustrating a test arrangement 500 for testing a fingerprint sensing device 110.

The method comprises arranging 702 a fingerprint sensing device 110 below the test module 100, moving 704 the test module 100 towards the fingerprint sensing device 110 such that the exterior surface portion 104 of the bottom element 102 makes contact with a sensing surface of the sensing device 110, capturing 704 an image using the fingerprint sensing device 110. Thereby, a functionality of the fingerprint sensing device can be tested using the described test module 100 and by analyzing the captured image, e.g. by comparing the captured image with an anticipated result corresponding to the pattern of the test module. A test sequence may also comprise capturing a plurality of images of the same pattern. For example, several images may be captured using different settings of the fingerprint sensing device.

Moreover, the test arrangement 500 may also comprise a plurality of consecutively arranged test modules 100 for testing different features or aspects of the fingerprint sensing device 110.

Even though the invention has been described with reference to specific exemplifying embodiments thereof, many different alterations, modifications and the like will become apparent for those skilled in the art. Also, it should be noted that parts of the test module may be omitted, interchanged or arranged in various ways, the test module yet being able to perform the functionality of the present invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A test module for testing a fingerprint sensing device comprising:
   an electrically conductive bottom element comprising an exterior surface portion configured to contact a sensing surface of said fingerprint sensing device;
   an electrically conductive intermediate element, connected to the bottom element on a side opposing said exterior surface portion, said intermediate element comprising a flexible material enabling said bottom element to change alignment in response to an applied force occurring when said exterior surface portion is pressed against a surface being tilted with respect to the exterior surface of the bottom element; and
   a top element configured connect the test module to a test fixture.

2. The test module according to claim 1, wherein said electrically conductive bottom element comprises a ground electrode configured to be connected to a corresponding ground electrode of a test fixture.

3. The test module according to claim 1, wherein said intermediate element is solid.

4. The test module according to claim 3, wherein said intermediate element consists of a single material.

5. The test module according to claim 1, wherein said intermediate element is hollow comprising flexible sidewalls.

6. The test module according to claim 5, wherein said flexible sidewalls are electrically conductive.

7. The test module according to claim 6, wherein said intermediate element comprises an electrically conductive fluid.

8. The test module according to claim 7, wherein said fluid is a gel.

9. The test module according to claim 1, wherein the electrical conductivity of the bottom element and of the intermediate element corresponds to the electrical conductivity of a finger.

10. The test module according to claim 1, wherein the exterior surface portion of the bottom element comprises a pattern configured to be detected by a fingerprint sensing device.

11. The test module according to claim 1, wherein the exterior surface portion of the bottom element comprises a pattern replicating a fingerprint.

12. The test module according to claim 1, wherein the exterior surface portion of the bottom element comprises a plurality of different patterns.

13. The test module according to claim 1, wherein said intermediate element is flexible in a direction perpendicular to the exterior surface portion of said bottom element.

14. The test module according to claim 1, wherein said bottom element is flexible having an elastic modulus which is higher than an elastic modulus of said intermediate element.

15. The test module according to claim 1, wherein the intermediate element comprises conductive rubber.

16. The test module according to claim 1, wherein the bottom element comprises conductive rubber.

17. The test module according to claim 1, further comprising an electrically conductive film arranged between the bottom element and the intermediate element, wherein the electrically conductive film is configured to be connected to a ground electrode of a test fixture.

18. A method for testing a fingerprint sensing device using a test module comprising:
   an electrically conductive bottom element comprising a substantially flat exterior surface portion configured to contact a sensing surface of said fingerprint sensing device;
   an electrically conductive intermediate element, connected to the first portion on a side opposing said exterior surface, said second portion comprising a flexible material enabling said bottom element to change alignment in response to an applied force occurring when said exterior surface is pressed against a surface being tilted with respect to the exterior surface of the bottom element; and
   a top element configured connect the test module to a test fixture, the method comprising:
      arranging a fingerprint sensing device below said test module;
      moving said test module towards said fingerprint sensing device such that said exterior surface portion of said bottom element makes contact with a sensing surface of said sensing device; and
      capturing an image using said fingerprint sensing device.

19. The method according to claim 18, further comprising verifying that the image captured by the fingerprint sensing device corresponds to a surface pattern of the exterior surface portion said bottom element.

* * * * *